Figure 1:
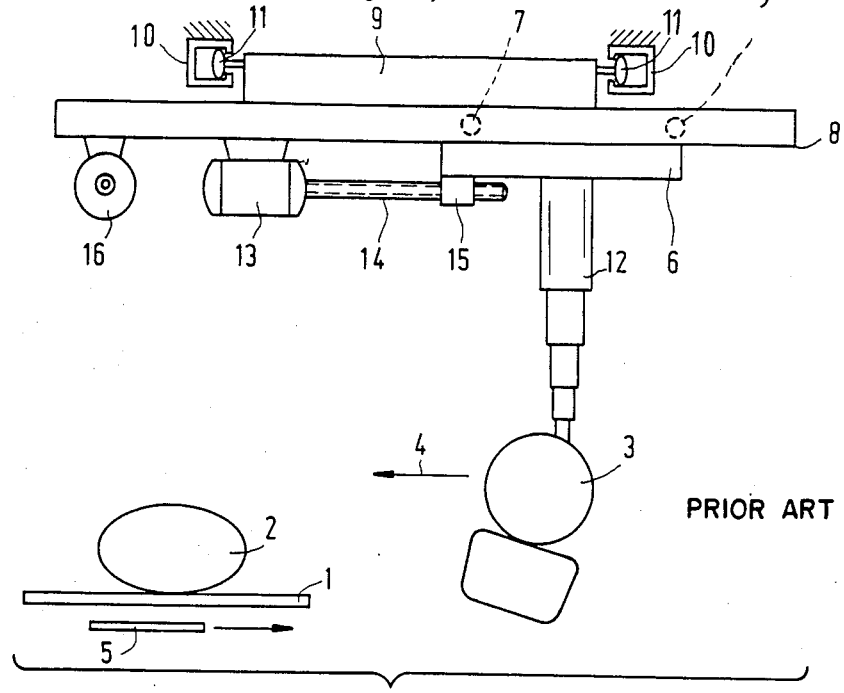

United States Patent [19]

Kunert

[11] Patent Number: 4,665,540

[45] Date of Patent: May 12, 1987

[54] APPARATUS FOR MAKING SECTIONAL RADIOGRAPHS

[75] Inventor: Heinz-Peter Kunert, Tangstedt, Fed. Rep. of Germany

[73] Assignee: U.S. Philips Corporation, New York, N.Y.

[21] Appl. No.: 746,213

[22] Filed: Jun. 18, 1985

[30] Foreign Application Priority Data

Jun. 22, 1984 [DE] Fed. Rep. of Germany ....... 3423001

[51] Int. Cl.$^4$ ............................................ G01N 23/00
[52] U.S. Cl. ....................................... 378/21; 378/25; 378/26; 378/27; 378/91
[58] Field of Search ....................... 378/21, 25, 27, 91, 378/22, 24, 26, 116

[56] References Cited

U.S. PATENT DOCUMENTS

| | | | |
|---|---|---|---|
| 3,714,427 | 1/1973 | Reiniger et al. | 378/25 |
| 3,777,124 | 12/1973 | Pavkovich | 378/91 |
| 3,777,145 | 12/1973 | Brunnett et al. | 378/91 |
| 3,792,334 | 2/1974 | Rouge | 378/27 |
| 4,139,776 | 2/1979 | Hellstrom | 378/91 |
| 4,211,927 | 7/1980 | Hellstrom et al. | 378/91 |

FOREIGN PATENT DOCUMENTS 2116705 10/1972 Fed. Rep. of Germany ........ 378/21
2154235 5/1973 Fed. Rep. of Germany .

Primary Examiner—Craig E. Church
Assistant Examiner—John C. Freeman
Attorney, Agent, or Firm—Jack E. Haken

[57] ABSTRACT

Apparatus for making sectional radiographs which allows for the operator to preset the scanning patterns to be followed by the apparatus during the making of a sectional radiograph. The operator positions the source or the image detector in at least one point on the path defining the desired scanning pattern. This position is measured and applied to an arithmetic device which derives therefrom reference values for driving the source and the image detector.

3 Claims, 2 Drawing Figures

APPARATUS FOR MAKING SECTIONAL RADIOGRAPHS

The invention relates to an apparatus for making sectional radiographs, comprising two drives for displacing an X-ray source and an image detector in two directions and also comprising a memory for the storage of sets of drive reference values which are associated with different scanning patterns; one of which can be fetched each time when a sectional radiograph is made.

An apparatus for making sectional radiographs which comprises two drives for displacing an X-ray source and an image detector in two mutually perpendicualr directions is already known from German Pat No. 36 915. Furthermore, from German Pat. No. 21 54 235 it is known to provide such an apparatus with a memory for storing the sets of drive reference values which are associated with the various scanning patterns; one of which can be fetched each time when a sectional radiograph is made.

The advantage of apparatus for making sectional radiographs which comprise two independent drives over such apparatus comprising only a single drive consists in that in principle any type of scanning pattern can thus be realized. In practice, however, these advantages cannot be fully utilized, so that only a comparatively small number of scanning patterns can be realized also by means of said apparatus. In order to initiate such a scanning pattern, the operator actuates a respective button after which a set of drive reference values which defines the relevant scanning pattern is fetched from the memory.

It is the object of the invention to construct an apparatus for making sectional radiographs of the kind set forth so that the operator himself oan preset scanning patterns or modify existing scanning patterns.

This object is achieved in accordance with the invention in that the source and the image detector can be positioned independently of the drive reference values stored, there being provided an actual value generator for determining the instantaneous position of the source and the image detector and also an arithmetic device for forming the drive reference values from the measured position values, it being possible to transfer the values calculated by the arithmetic device to the memory which is constructed as a read/write memory.

Thus, the operator positions (manually or by means of a motor drive) the source or the detector in a point on the path to be followed by the source or the detector. From the actual values measured in these points the arithmetic device forms a set of drive reference values which is transferred to the read/write memory. These values can be fetched therefrom at a later instant for controlling the drives in such a manner that the source and the detector follow the path preset by the operator.

In a further embodiment in accordance with the invention, the arithmetic device forms from a predetermined type scanning pattern and one or a few positions of the source a set of drive reference values for a scanning pattern of the preset type which extends in accordance with the preset position or positions. The desired type of scanning pattern, for example a circular, elliptical, helical or linear displacement, is then preselected by the operator (on the control console of the apparatus). Subsequently, the parameters of the selected pattern are adjusted by positioning the source. In the case of a circular pattern, for example, such a parameter is the radius which corresponds to the distance between the source or the detector and its central position. In the case of another scanning pattern, more parameters must be preset by the operator; for example, in the case of an elliptical pattern it is necessary to preset the length of the long and the short semi-axis. From the parameters thus preset the aritlmetic device forms a set of drive reference values which can be fetched at a later instant again. The type of pattern is thus preset and the operator can only influence individual parameters of this scanning pattern.

Figure 2:
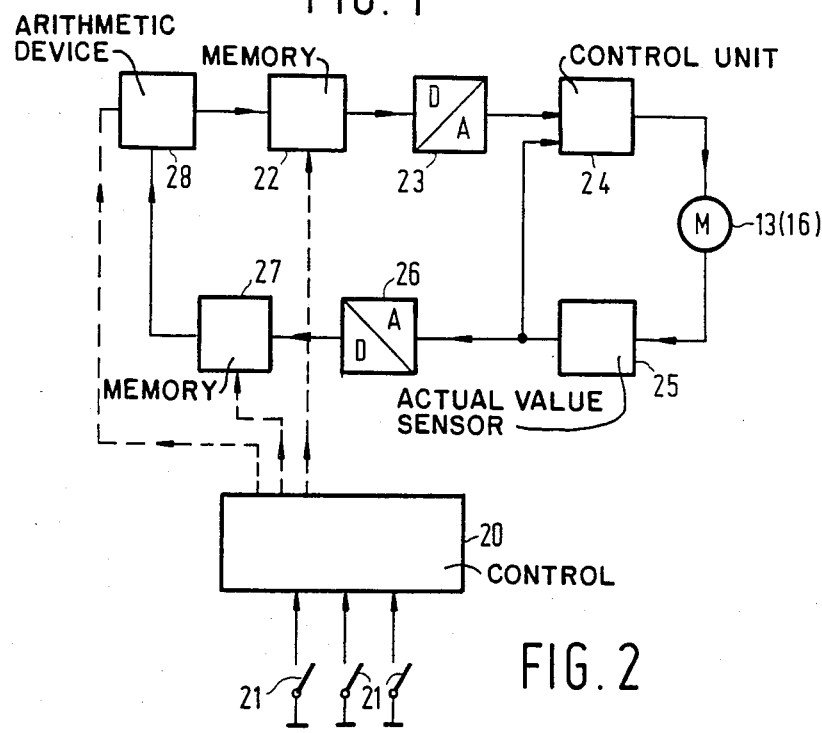

However, in another embodiment in accordance with the invention, the arithmeic device forms the scanning patterns from a plurality of position values. This embodiment allows for the operator to adjust completely new scanning patterns. The operator then moves the source or the detector along a path to be followed by these components at a later stage and the relevant path is stored by the storage of the actual values associated with the various points on the path. The arithmetic device thus links the points on the path to a constant scanning pattern. The invention will be described in detail hereinafter with reference to the drawings. Therein:

FIG. 1 shows the mechanical construction of an apparatus for making sectional radiographs in which the invention can be used, and FIG. 2 shows a circuit diagram of the invention.

FIG. 1 shows the short side of a table 1 of an apparatus for making sectional radiographs, an object 2 being positioned on said table. The object 2 is irradiated by an X-ray source 3 which can be displaced in the direction of the arrow 4 as well as perpendicularly to the plane of drawing, the central ray of the X-ray source always remaining aimed at the same point of the object. Using a connecting rod (not shown), the X-ray source is coupled to a film cassette 5 underneath the table 1 in such a manner that the X-ray source and the film cassette 5 are moved in opposite directions.

The X-ray source 3 is supported by a telescopic ceiling support 12 which is connected to a transverse carriage 6 which is arranged to be displaceable on rails 8 by means of rollers 7 in a direction perpendicular to the longitudinal axis of the table, said rails being connected to a longitudinal carriage 9 which itself is arranged to be displaceable by means of rollers 11 on rails 11 secured to the ceiling, in a direction parallel to the longitudinal axis of the table 1. The longitudinal carriage 9 is provided with a motor 13 which drives a spindle 14 which engages an internally threaded member 15 provided on the transverse carriage 6. In this way the transverse carriage 6 can be displaced by the motor either to the left or to the right in accordance with the direction of rotation of the spindle. A further motor 16, rigidly secured to the longitudinal carriage, engages in the same way, via a spindle, an internally threaded member (not shown) which is secured to the ceiling, so that the longitudinal carriage can be displaced by the motor in the direction at right angles to the plane of drawing.

FIG. 2 shows a circuit diagram of the electronic control circuitry for one of the motors 13 or 16. In a first mode of operation which is selected by the operator by actuation of one of the switches 21, a control device 20 fetches a first set of reference values associated with a given scanning pattern from a memory 22. These reference values are continuously applied, via digital/analog converter 23, to a control unit 24 which controls the motor 13 or 16, said reference values being compared with the values values supplied by an acutal value sensor 25. The X-ray source 3 and the image detector 5 that follow a predetermined scanning pattern.

In addition to this mode of operation, the source or the image detector can be displaced manually or with a motor to a given position, independent of a preset scanning pattern. The actual value sensor 25 which generates a signal corresponding to the distance between the source and a central position thereof and which may be a position sensor which is coupled, for example, to the drive spindle of the motor 13 or 16, supplies a signal which is digitized by an analog/digital converter and which is stored in a memory 27. This signal is representative of the relevant actual position value and is further processed by an arithmetic device 28 so that (possibly after the processing of a number of further actual position values) a set of position reference values associated with a new scanning pattern is applied to the read/write memory 22. An existing scanning pattern can thus be modified or a completely new scanning pattern can be created.

When merely an existing scanning pattern is to be modified, i.e. when its parameters are to be modified, it will only be necessary to position the source or the image detector to one or a few points on the path of the modified scanning pattern. For example, when a circle is to be modified into a circle having a different radius, it will merely be necessary to move the source cone to a position which is situated at a distance from the central position which corresponds to the radius of the new circle. The arithmetic device 22 then averages the set of reference values "circle" stored in the memory 22 (by multiplying all reference values by a constant factor) in such a manner that when this set of reference values is fetched at a later stage, the source and the detector will follow a circular path whose radius corresponds to the distance between these components and the central rest position (in which the source and the detector are situated on a straight line perpendicular to the plane of the section) in this newly programmed scanning pattern.

However, it is also possible to form completely new scanning patterns. In that case the operator must position the source and the detector in a plurality of points on the path of the desired scanning pattern. From the actual position values thus obtained which are stored in the intermediate memory 27, the arithmetic device 28 forms a set of position reference values. When this set is fetched at a later stage, the source and the detector will follow a scanning pattern which extends through the previously determined points on the path.

What is claimed is:

1. In apparatus for making sectional radiographs of the type which comprises a movable X-ray source, a movable X-ray detector, means which couple motion of the X-ray source with motion of the X-ray detector to produce sectional radiographs of a plane through an object, means which store data describing one or more possible paths for motions of the X-ray source and detector, and means for driving the motions of the X-ray source and detector in two independent directions in response to the stored data; the improvement comprising:

means which permit an operator to displace the source and detector to new positions independently from previously stored data and which store new position data determined by the new positions of the source and detector and means which calculate data which describes a new path for said motion using the stored new position data parametrically.

2. The apparatus of claim 1 wherein the new path is a circle and the means which calulate utilize the new position data parametrically as the radius of said circle.

3. The apparatus of claim 1 wherein the new path is an ellipse and the means which calculate utilize the new position information parametrically as the major and minor radii of the ellipse.

* * * * *